US005789384A

United States Patent [19]
Khavinson et al.

[11] Patent Number: 5,789,384
[45] Date of Patent: Aug. 4, 1998

[54] PHARMACEUTICAL DIPEPTIDE COMPOSITIONS AND METHODS OF USE THEREOF

[75] Inventors: Vladimir Khatskelevich Khavinson; Sergy Vladimirovich Sery; Vyacheslav Grigorievich Morozov, all of St. Petersburg, Russian Federation

[73] Assignee: Cytran, Incorporated, Kirkland, Wash.

[21] Appl. No.: 415,099

[22] Filed: Mar. 31, 1995

Related U.S. Application Data

[63] Continuation of Ser. No. 271,386, Jul. 6, 1994, abandoned, which is a continuation of Ser. No. 26,341, Mar. 4, 1993, abandoned.

[51] Int. Cl.$^6$ .................................................. A61K 38/00
[52] U.S. Cl. ............................... 514/19; 514/9; 514/11; 514/12; 514/13; 514/14; 514/15; 514/16; 514/17; 514/18
[58] Field of Search ........................ 514/9, 11–19

[56] References Cited

U.S. PATENT DOCUMENTS

| 4,079,127 | 3/1978 | Goldstein et al. |
| 4,389,343 | 6/1983 | Horecker |
| 4,396,605 | 8/1983 | Birr |
| 4,466,918 | 8/1984 | Birr et al. |
| 4,752,602 | 6/1988 | Lipsky et al. |
| 4,910,296 | 3/1990 | Birr et al. |
| 5,036,052 | 7/1991 | Ozeki et al. ............... 514/19 |
| 5,143,903 | 9/1992 | Polita et al. ............... 514/18 |
| 5,538,951 | 7/1996 | Morozov et al. |

FOREIGN PATENT DOCUMENTS

| 0 346 501 | 12/1989 | European Pat. Off. |
| 1748827 | 7/1992 | U.S.S.R. |
| WO 92/17191 | 10/1992 | WIPO |
| WO 93/08815 | 5/1993 | WIPO |

OTHER PUBLICATIONS

Rodionov et al, Vestn. Dermatol., Venerol. vol. 1, pp. 42–45 (1990).
Cecil Textbook of Medicine, 19th edition, pp. 1785–1796, 1992.
Low et al., PNAS, 78, 1161–1166 (1981).
*Experientia,* vol. 42, No. 5, May 1986, Basel Ch. pp. 522–530, G.H. Werner et al., 'Immunomodulating peptided'.
Goodman & Gilman, *"The Pharmacological Basis of Therapeutics"* 6th Ed. App III pp. 1738–1740, (1980).
Dayhoff, *"Atlas of Protein Sequence and Structure"* vol. 5 (1972) pp. 89–99.
Ho, Science vol. 272 p. 1124, May 1996.
Mellors et al, Science vol. 272 p. 1167, May 1996.
Fox, Biotechnology vol. 12 p. 178, Feb. 1994.
Haynes et al, Ann. Med. vol. 28 p. 39, 1996.

*Primary Examiner*—Sheela Huff
*Attorney, Agent, or Firm*—Townsend and Townsend and Crew, LLP

[57] ABSTRACT

Methods are provided for the therapy of immunodeficient, immunodepressed or hyperactive immune states and for the treatment of opportunistic infections in such states comprising administering to a subject a pharmaceutically acceptable composition comprising as an active ingredient the dipeptide L-Ile-L-Trp, linear and cyclic monomers and polymers thereof, and/or pharmaceutically acceptable salts thereof.

61 Claims, No Drawings

PHARMACEUTICAL DIPEPTIDE COMPOSITIONS AND METHODS OF USE THEREOF

This application is a continuation of application Ser. No. 08/271,386, filed Jul. 6, 1994, abandoned, which is a continuation of application Ser. No. 08/026,341, filed Mar. 4, 1993, abandoned.

The present invention is directed to dipeptide pharmaceutical compositions and uses thereof, in particular, uses thereof for treatment of immunodepressed states and of opportunistic infections in immunodepressed states.

BACKGROUND OF THE INVENTION

Several polypeptides found in the thymus gland have been implicated as playing roles in the development and maintenance of immunological competence in animals, including human beings. Some of these polypeptides have been shown to stimulate the maturation, differentiation and function of T-cells. For example, a heat-stable fraction isolated from calf thymus extracts, designated as Thymosin fraction 5, has been shown to reconstitute immune functions in thymic-deprived or immunodepressed individuals. Several peptides have been isolated from Thymosin fraction 5, such as Thymosin alpha$_1$(28 amino acids, U.S. Pat. No. 4,079,127), Thymosin beta$_4$ (44 amino acids, Low et al., PNAS, 78,1162 –1166 (1981)), Thymosin beta$_8$ (39 amino acids, U.S. Pat. No. 4,389,343) and Thymosin beta$_9$ (41 amino acids, U.S. Pat. No. 4,389,343). However, practical administration of such polypeptides is expensive due to the relatively low yield and complexity of isolation and/or manufacture of such long chain polypeptides. Most importantly, in some cases, these polypeptides produce side reactions in patients.

The present invention is based in part on the discovery that a dipeptide, L-Ile-L-Trp, including linear or cyclic forms of this dipeptide or polymers thereof, exhibit a broad range of efficacy for prevention and treatment of opportunistic infections in immunodepressed states, and for therapeutically effective treatment of immunodeficient states. This is believed to be highly unexpected for such a relatively small compound to exhibit such a broad range of activity. Furthermore, we have not found any significant side effects from the use of the dipeptide according to the present invention. Due to its simple nature, the dipeptide is rather inexpensive to manufacture.

As used herein, the terms "immunomodulator" and "immunomodulating" encompass the activity of enhancing or restoring the subject's immune system, as evidenced by measurable blood parameters and/or the patient's improved ability to combat infection or disease, and the ability to heal tissue. Hence, immunomodulation encompasses improvement of the immune system due to an immunodeficient state (for example, caused by removal of the thymus), and/or an immunodepressed state (for example, caused by exposure to radiation). Furthermore, the present invention provides for modulation of the immune system by lowering blood parameters and other indicia of the immune state if these indicia are abnormally elevated. The present invention encompasses the therapeutic method of treating the immunodeficient, immunodepressed or elevated immune state per se, thus providing prophylaxis against infection and disease, as well as a treatment of infection, disease or wound indirectly by enhancing the immune system.

It is therefore an object of the present invention to provide pharmaceutical compositions of the L-Ile-Trp dipeptide which have broad immunomodulating activity, as well as activity for other uses such as treatment of infections, disease and wounds (burns, frost bites, and the like), enhancement of metabolic processes, and many other uses.

It is an object of the present invention to provide therapeutic methods for treatment of immunodepressed and immunodeficient states.

It is yet another object of the present invention to provide methods for preventing and treating opportunistic infections in immunodeficient and immunodepressed states.

These and other objects will be apparent from the following description and appended claims.

DESCRIPTION OF THE PREFERRED EMBODIMENTS

The present invention provides pharmaceutical preparations comprising the dipeptide L-Ile-L-Trp (SEQ. ID. NO. 1), using the normal convention wherein the first named amino acid is the amino terminus and the last named amino acid is the carboxyl terminus.

The simplest cyclic form of the dipeptide is the cyclized monomer

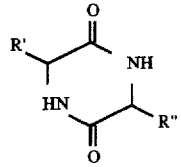

wherein R' and R" are the respective α-side chains of the Ile and Trp. Dimers, trimers, etc. are also contemplated by the present invention, e.g., (SEQ. ID. NOS. 2–4) either in linear form, such as,

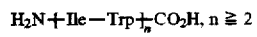

or in cyclic form, such as,

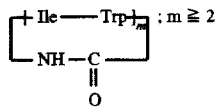

The compositions according to the present invention may be formulated into any convenient formulation which allows for the active ingredient to be absorbed into the blood stream. Intramuscular and intranasal forms of application are preferred. The preferred dosage rate of the active ingredient for intramuscular administration is about 50 to 100 μg per dose for adults (for a 300 to 1000 μg total treatment therapy); for infants up to 1 year old about 10 μg per dose, for infants 1 to 3 years old about 10 to 20 μg per dose; for infants 4 to 6 years old about 20 to 30 μg per dose, for children 7 to 14 years old about 50 μg per dose. All of the foregoing dosages are useful for a treatment of 3 to 10 days, depending upon the immunodeficiency level. The treatment may be repeated as needed, usually within 1 to 6 months.

For prophylactic uses against opportunistic infections in immunodeficient or immunodepressed patients, the intramuscular and/or intranasal single daily dose for adults may be from about 50 to 10 μg, and for children about 10 to 50 μg per dose for treatment over 3 to 5 days.

For treatment of burns, frost bite, or other wounds, including chronic apical periodontitis, the dipeptide may be applied in about 100 μg doses as a paste or other suitable medium.

For ophthalmology, such as for treatment of infectious eye diseases, the dipeptide may be applied in single daily dosages of about 10 µg (over 4 to 10 days) or as installations into the conjunctival cavity at about 5 µg twice daily over about 4 to 5 days.

The dipeptide may be utilized intramuscularly as an injection solution with the active ingredient in a therapeutically effective immunopotentiating amount of about 0.001 to 0.01% by weight. If presented in the form of a tablet, capsule or suppository it is preferred that the active ingredient be present in an amount of about 0.1 mg per tablet, suppository or capsule. If presented in such form, the capsule, suppository or tablet may also contain other conventional excipients and vehicles such as fillers, starch, glucose, etc.

The dipeptide may be obtained by conventional peptide synthesis, including the Merrifield solid state peptide synthesis technique. Typically an amino and side chain protected derivative of an activated ester of glutamic acid is reacted with protected L-tryptophan. After elimination of the protecting groups and conventional purification, such as by thin layer or GL chromatography, the peptide may be purified such as by, lyophilization, gel purification, and the like.

The purified dipeptide L-Ile-L-Trp, comprises a white powder.

The active dipeptide ingredient of the pharmaceutical preparations according to the present invention may be used as a free peptide or in the form of a water soluble pharmaceutically acceptable salt, such as a sodium, potassium, ammonium or zinc salt. It will be understood that the dipeptide may be administered with other active ingredients which independently impart an activity to the composition, such as, antibiotics, interferon, anesthetics, and the like.

The most preferred formulation according to the present invention is a solution for intramuscular injection containing about 0.001 to 0.01% by weight (.0001-.001mg/kg body weight, or 10–100 µg active ingredient per 1 ml solvent). The pharmaceutically acceptable vehicle for this injection form may be any pharmaceutically acceptable solvent such as 0.9% aqueous sodium chloride, distilled water, Novocaine solution, Ringer's solution, glucose solution, and the like. The dipeptide containing compositions according to the present invention may be administered in a compatible pharmaceutical suitable for parenteral administration (e.g., intravenous, subcutaneous, intramuscular). The preparations may be subjected to conventional pharmaceutical operations, such as sterilization, and may contain adjuvants, such as preservatives, stabilizers, wetting agents and the like.

The pharmaceutical preparations according to the present invention demonstrate a high effectiveness in the treatment of immunodepressed and immunodeficient states for the preventing and treatment of opportunistic infections in those states. Also included within the scope of the present invention are the pharmaceutically acceptable salts of the dipeptide, such as sodium or potassium or strong organic bases, such as guanidine.

The dipeptide containing compositions according to the present invention have activity in the restoration and stimulation of the immune functions. Thus they are useful in the treatment of opportunistic infections of an immunodepressed subject in an immunopotentiating effective amount as described above.

The dipeptide compositions according to the present invention may also be used in veterinary practice as an immunomodulatory agent for prophylaxsis and treatment of hypotrophy in farming animals, fur bearing animals and poultry.

Among the opportunistic infections which may be treated utilizing the compositions according to the present invention are: respiratory diseases, influenza, AIDS, burns, wounds, other open sores, rashes (due to allergic reactions), sun exposure, local trauma (with an ointment), eczemas, psoriasis, and the like. Furthermore, the compositions according to the present invention may be utilized to assist healing in immunodepressed or immunodeficient states, such as for the healing of bone fractures, lesions, gingival diseases, gynecological infections, infralymphatic infections, and the like. The compositions may also be used to enhance the immunodeficient state to increase susceptibility to microbial antibiotics and to enhance the patient's responsive reaction to other types of therapies.

The compositions according to the present invention also may be utilized to enhance metabolic processes; to enhance production of blood insulin; for treatment of irradiated cancer patients, as well as for veterinary uses.

The following examples are provided to further elucidate the invention, but are not intended to restrict the invention in scope or spirit in any way.

EXAMPLE 1

Individuals infected with AIDS are treated with Ile-Trp. This dipeptide is an effective cell mediator, restoring normal immunologic indices, including T-cell functional activity and T4/T8 ratios. Method of Administration: Sterile saline containing the sodium salt of the medication is administered either IM, infralymphatically, or intranasally each day for 5–10 days consecutively every 30 days.

Immunosupressed individuals who have sustained radiation injuries are treated with Ile-Trp with excellent restoration of immunological indices and models for acquired immune deficiency syndrome. Ile-Trp may thus benefit AIDS infected individuals by reducing the need to use other medications with toxic side effects, and sustain and or support the individuals by reducing the needs to use other medications with toxic side effects, and sustain and or support the individuals immune indices resulting in a reduction of opportunistic infections.

EXAMPLE 2

Patients with pyoderma, including furunculitis, cellulitis, and folliculitis, are treated with Ile-Trp Trp with a control group which is not treated with Ile-Trp. Medications are administered either IM or intranasally for 5 consecutive days. Immunological indices are normalized with disappearance of skin manifestations and relapses are prevented after treatment with Ile-Trp. Clinical improvement correlate with immunological indices correction. Administration IM, intranasally, or topically as a sterile saline solution of medication for a period of 5 to 10 days at a concentration of 1 µg/kg body weight.

EXAMPLE 3

A number of patients within the group patients afflicted with furunculitis, pyoderma, cellulitis, and folliculitis are afflicted with acne vulgaris and acne. The immunological indices are corrected and normalized rapidly within the group therapy. The clinical outcome correlates with the correction of immunological indices, and relapses are controlled.

EXAMPLE 4

Patients with psoriasis are treated with Ile-Trp and some patients are used as controls. The administration of 100 µg IM or intranasally for a period of 10 days results in the improvement in most of the patients, and total recovery in some of the patients.

EXAMPLE 5

Female patients with the various disorders (pelvic inflammatory diseases, cervicitis, vaginitis and various tubo-ovarian and adnexal abscesses) are treated and some patients are used as controls. Ile-Trp is applied IM, intranasally at 100 µg 5 consecutive days or 50 µg intralymphatically for 5 consecutive days in conjunction with conventional therapy. The clinical effect of Thymogen expresses the arresting of pain syndrome, the control of body temperature, e.g. reduction of fever, the decrease of duration of conventional treatment. The normalization of immune status correlates with clinical improvements.

EXAMPLE 6

Patients treated with Ile-Trp either topically, IM, or intranasally experience marked reduction of recurrence of herpetic lesions, with substantial reduction in the period between outbreaks. Treatment with Ile-Trp in combination with interferon also shows a lessening of lesion outbreaks.

EXAMPLE 7

Patients with Herpes Zoster are treated with Ile-Trp in combination with conventional interferon treatment and some control patients with interferon alone. Administration single daily IM or intranasal 100 µg during a period of 10 days results in accelerated regression of foci of herpetic infection. There is noted prevention of relapses, and some healing occurred earlier than control groups. Immunological indices correlates with clinical outcome.

EXAMPLE 8

Patients are treated for gingival disease by subcutaneous administration of Ile-Trp in the area of the gingiva. The treatment results in the arresting of gingival disease. Administration of 100 µg Im, subcutaneously, or by electrophoresis (whereby a small voltage charge to the gums results in a rapid transfer of medication through the gum epithelium) results in the arresting of bleeding, more rapid restoration of inflammatory processes, and the decrease of purulent discharge. The treatment results in fewer recurrences and prolongation of normal gums.

EXAMPLE 9

The treatment with toothpaste containing Ile-Trp will result in a reduction of dental caries.

EXAMPLE 10

Patients with periapical granulomas treated with Thymogen are tested. Instillation of 100 µg of Ile-Trp into the foramen at the base of the tooth, or in the composition of the filling paste during 3 days results in the accelerated arrestation of the inflammatory process, reduction in pain, and increases stability of the underlying dental structures as evidenced by x-ray studies.

EXAMPLE 11

The use of dental toothpaste containing Ile-Trp will result in the reduction of gingival disease and reduction in dental caries.

EXAMPLE 12

The use of Ile-Trp 100 µg IM, intranasally, or intralymphatically controls the advance of lymphangitis.

EXAMPLE 13

Patients with acute respiratory disease, including upper airway diseases, such as colds, are treated with Ile-Trp. Administration IM or intranasally 100 µg 3 –7 days results in a milder course of the viral infection. Secondary infectious complications are diminished, and the duration of the treatment is also diminished.

EXAMPLE 14

Patients are treated with Ile-Trp, administration IM, intranasally, and installation into sinuses with 1 µg/kg dose during a period of 3 –10 days results in normalization of nasal breathing, the disappearance of nasal mucous swelling, the arresting of exudates from affect sinuses, and improved general condition and immune status.

EXAMPLE 15

Ile-Trp IM or intranasal accompanying conventional therapy (antibiotics) results in accelerated healing of chronic and acute ear infections.

EXAMPLE 16

Patients with various eye problems are treated by conventional methods, with one group receiving Ile-Trp in addition to the conventional treatment. Administration of Ile-Trp intra ocularly at 18 µg for 5 consecutive days, or as installation into conjunctival cavity as drops bid for 5 days results in more rapid arresting of the inflammatory process and the increase in visual acuity, and the decrease of duration of treatment.

EXAMPLE 17

Patients treated with Ile-Trp and patients in the control group, are administered medication IM or intranasally 100 µg 5 –10 days resulting in accelerated reduction in symptom complexes including joint pain, muscle aches, fevers, chills, and upper respiratory symptoms.

EXAMPLE 18

Ile-Trp administration IM or intranasally results in the improved immune parameters, functional activity of lymphocytes and neutrophils, and reduction of post-operative complications and infections associated with bone-marrow compromise, such as, that caused from transplant or radiation exposure.

EXAMPLE 19

Patients afflicted with various allergies as described and patients in a control group are treated with Ile-Trp in dose 1 µg/kg IM or intranasally for 5 –7 days results in disappearance of allergic reactions.

EXAMPLE 20

Patients exposed to massive hemotransfusions during post-operative period are treated with Ile-Trp. The peptide is administered starting from 4–6 day of post-operative period single daily IM or intranasally in doses 100 µg for 5 days. Treated patients do not show clinical manifestation of allogeneic rejection while some of the control patients show hemotranfusional reactions.

EXAMPLE 21

Ile-Trp is applied in patients treated with antibiotics for various indications who have unfavorable allergological history. Ile-Trp is administered IM or intranasally single daily at 100 µg for 5–10 days. The use of Ile-Trp prevents the arising of allergic reactions or promotes the less severe course in most cases.

EXAMPLE 22

Ile-Trp is administered to patients subjected to skin grafting. Ile-Trp is administered IM or intranasally single daily at 50–100 µg for 5 days. In the tested patients the use of Ile-Trp prevents the arising of infections complications and graft rejection.

EXAMPLE 23

Ile-Trp is administered to patients suffering from chronic skin diseases caused by antibiotic-resistant staphylococci. Ile-Trp is administered IM in single daily doses of 100 µg for 5 days and intranasally to a different group in the same daily and total dose. In the patients with signs of secondary T-immunodeficiency the staphylocci antibiotic- sensitivity to one, few or all antibiotics is increased which then permits one to choose for each patient an effective antibiotic with exclusively high activity against a given pathogen.

EXAMPLE 24

Ile-Trp is used in patients with wounds of various origin, type and localization. Ile-Trp is administered IM or topically single daily at 100 µg for 10 days. The use of the dipeptide speeds up (when compared to the control group) significantly wound healing, reduces therapy duration and prevents the development of infectious complications.

EXAMPLE 25

Administration of Ile-Trp either intranasally or IM accelerates wound healing, resulting in statistically fewer infections and reduced escar.

EXAMPLE 26

Ile-Trp is applied to patients with bone fractures of various origin, type and localization. Ile-Trp is administered intramuscularly or intranasally single daily at 100 up for 10 days. The use of the dipeptide accelerates essentially (in comparison with the control group) the consolidation of fractures, prevents the development of infectious complications, reduces pain syndrome and treatment duration.

EXAMPLE 27

Ile-Trp is prescribed to patients with chronic osteomyelitis of various ethiology and localization. Ile-Trp is administered IM or intranasally single daily at 100 ug for 10 days. The use of the peptide renders a pronounced positive influence on clinical course, expressed by a significant decrease of intoxication syndrome and pain syndrome, disappearance of purulent inflammatory manifestations, speeding up of wound healing, reduction of destruction areas, prevention of relapses.

EXAMPLE 28

Patients with cutaneous burns are treated with Ile-Trp either IM or intranasally. Accelerated wound healing, diminished frequency of infections, and less escar are noted in those individuals treated with the peptide.

EXAMPLE 29

Patients with frostbite to the extremities are treated with Ile-Trp either IM or intranasally. Rapid healing and restoration of tissue integrity is observed.

EXAMPLE 30

Ile-Trp administration either IM or intranasally results in less deformity and scarring evidenced by experience in healing fractures, burns, military accidents, and other injuries to the extremities.

EXAMPLE 31

Patients treated with Ile-Trp simultaneously during the administration of chemotherapy experience fewer complications and side effects related to chemotherapy including diminished frequency and intensity of ulcerative lesions, nausea, and other related problems of chemotherapy administration.

EXAMPLE 32

Ile-Trp is applied to persons in combination with the anti-flu vaccination delivered by air pressure. The Ile-Trp dose is 50 ug delivered in a single dose for 3 consecutive days. After Ile-Trp use, a significant decrease of sickness rate for a period of 12 months is observed compared to controls who receive flu-vaccination without the peptide.

EXAMPLE 33

Ile-Trp is applied in pregnant women with Toxemia of first and second half of pregnancy. Ile-Trp is administered IM and intranasally at 100 ug daily for 5–10 days. It is observed that the BP normalized, and peripheral edema is reduced with normalization of the blood chemistry profile, and the restoration of initially altered immunologic indices.

EXAMPLE 34

Ile-Trp is administered to pregnant women. The route of administration is IM or intranasally 100 ug daily for 5–10 days. Signs of clinical improvement are resolution of weakness, dizziness, and increased appetite, and the normalization of the immunological and hematological indices.

EXAMPLE 35

Patients with pyelonephritis are treated with the administration of Ile-Trp in a single daily dose of 100 ug for 5–10 consecutive days in combination with conventional therapy which results in reduction of fever, the normalization of urine analysis, and the improvement and resolution of the infection.

EXAMPLE 36

Patients with leprosy (Hansen's disease) are treated with Ile-Trp IM or intranasally in single daily doses of 100 ug for 5 days consecutively in additional to conventional therapy. Administration results in resolution of the lesions and prevented relapses, and promotes more rapid healing of specific ulcers.

EXAMPLE 37

Patients are studied who have relapsing forms of tropical malaria, moderate to severe, and severe cases with 21 patients in the control group. Ile-Trp is administered at 100 ug single daily doses IM or intranasally for 5–10 days. The results of such treatment are reduction of hepatolineal syndrome, the normalization of hematological and immunological indices, reduction of fever, and prevention of relapses.

EXAMPLE 38

Ile-Trp is applied in patients with hemorrhagic Dengue Fever. Ile-Trp is administered IM single daily doses of 100 ug for 5 consecutive days in conjunction with conventional therapy. The results of treatment are reduction in fever, reduction of toxic symptoms, significant decrease in hepatolineal syndrome.

EXAMPLE 39

Patients infected with pulmonary TB are studied and treated. Ile-Trp is administered at 50 to 100 ug every other day during 5 doses total in combination with convention therapy. The results of the treatment several months after treatment reveal the disappearance of toxic symptoms, the reabsorption of infiltrates, and resolution of pulmonary cavities.

EXAMPLE 40

Patients, children and adults, with bronchial asthma are studied. Ile-Trp was administered IM single daily doses 1 ug/kg for 5-10 days resulting in less severe clinical symptoms. A significant reduction in bronchial obstruction and laryngotracheitis is noted. The normalization of fever, and the reduction in duration of treatment is noted.

EXAMPLE 41

A total 125 patients infected with Shigella dysentery are examined. Ile-Trp is administered IM single doses of 100 ug for 10 consecutive days with resultant normalization of fever, the reduction of toxemia, and the normalization gastrointestinal disorders and symptoms.

---

What is claimed is:

1. A method for treating an immunodeficient, immunodepressed or hyperactive immune state in a subject comprising administering to the subject an immunomodulating amount of L-Ile-L-Trp, cyclized L-Ile-L-Trp, a linear or cyclic polymer of L-Ile-L-Trp, or a pharmaceutically acceptable salt of any of the foregoing.

2. The method of claim 1 comprisig administering to the subject a linear or cyclic dimer or trimer of L-Ile-L-Trp in an amount effective for immunomodulation.

3. The method of claim 1 comprising administering to the subject L-Ile-L-Trp in an amount effective for immunomodulation.

4. The method of claim 3 wherein the subject suffers from an immunodeficient or immunodepressed state.

5. The method of claim 4 wherein the subject has been subject to thymectomy.

6. The method of claim 4 wherein the subject has an immunodepressed state resulting from exposure to radiation.

7. The method of claim 4 wherein the subject has an immunodepressed state resulting from exposure to radiation in the treatment of cancer.

8. The method of claim 3 wherein the subject suffers from eczema.

9. The method of claim 3 wherein the subject suffers from psoriasis.

10. The method of claim 3, wherein the subject suffers from allergy.

11. The method of claim 30 wherein the subject suffers from bronchial asthma.

12. A method for the therapeutic treatmnent of an infections disease in a subject comprising admitistering to the subject an immunopoteatiating amount of L-Ife-L-Trp, cyclized L-Ile-L-Trp, a linear or cyclic polymer of L-Ile-L-Trp, or a pharmaceutically acceptable salt of any of the foregoing.

13. The method of claim 12 comprising administering to the subject an immunopotentiating amount of a linear or cyclic dimer or trimer of L-Ile-L-Trp.

14. The method of claim 12 comprising administering to the subject an immunopotentiating amount of L-Ile-L-Trp.

15. The method of claim 14 wherein the disease results from viral infection.

16. The method of claim 15 wherein the infection is HIV infection.

17. The method of claim 15 wherein the infection is herpes infection.

18. The method of claim 15 wherein the infection is herpes Type I or Type II infection.

19. The method of claim 15 wherein the infection is Herpes Zoster infection.

20. The method of claim 15 wherein the infection is influenza virus infection.

21. The method of claim 15 wherein the infection is influenza virus category Type A or Type B infection.

22. The method of claim 15 wherein the infection is Hepatitis A or Hepatitis B infection.

23. The method of claim 15 wherein the disease is hemorrhagic dengue fever.

24. The method of claim 14 wherein the disease results from bacterial infection.

25. The method of claim 24 wherein the disease is Hansen's disease.

26. The method of claim 24 wherein the disease is typhus of the para A and B category.

27. The method of claim 24 wherein the disease is tuberculosis of the lung.

28. The method of claim 24 wherein the disease is yersenia, pseudo-tuberculosis.

29. The method of claim 24 wherein the disease is Shigella dysentery.

30. The method of claim 14 wherein the disease results from parasitic infection.

31. The method of claim 30 wherein the disease is malaria.

32. The method of claim 14 wherein the disease is a skin infection.

33. The method of claim 32 wherein the disease is pyoderma, furunculitis or cellulitis.

34. The method of claim 32 wherein the disease is acne.

35. The method of claim 14 wherein said disease results from infralymphatic infection.

36. The method of claim 14 where the disease is lymphangitis.

37. The method of claim 14 wherein the disease results from a gynecological infection.

38. The method of claim 37 wherein the disease is pelvic inflammatory disease.

39. The method of claim 37 wherein the disease is cervicitis.

40. The method of claim 37 wherein the disease is vaginitis.

41. The method of claim 37 wherein the disease is tubo-ovarian abscess.

42. The method of claim 37 wherein the disease is adnexal abscess.

43. The method of claim 14 wherein the disease is an acute respiratory disease.

44. The method of claim 14 wherein the disease is sinusitis or parsinusitus.

45. The method of claim 14 wherein the disease is Otitis media.

46. The method of claim 14 wherein the disease is conjunctivitis, uveitis, and keratitis.

47. The method of claim 14 wherein the disease is dental caries.

48. The method of claim 14 wherein the disease is gingival disease.

49. The method of claim 14 wherein the disease is periapical granuloma.

50. A method for the therapeutic treatment of tissue damage in a subject comprising administering to the subject an immunopotentiating amount of L-Ile-L-Trp, cyclized L-Ile-L-Trp, a linear or cyclic polymer of L-Ile-L-Trp, or a pharmaceutically acceptable salt of any of the foregoing.

51. The method of claim 50 comprising administering to the subject an immunopotentiating amount of a linear or cyclic dimer or trimer of L-Ile-L-Trp.

52. The method of claim 50 comprising administering to the subject an immunopotentiating amount of L-Ile-L-Trp.

53. The method of claim 52 wherein the tissue damage results from a burn.

54. The method of claim 52 wherein the tissue damage results from frost bite.

55. The method of claim 52 wherein the tissue is corneal tissue.

56. A method for treating toxemia or anemia in a subject during pregnancy comprising administering to the subject an immunopotentiating amount of L-Ile-L-Trp, cyclized L-Ile-L-Trp, a linear or cyclic polymer of L-Ile-L-Trp, or a pharmaceutically acceptable salt of any of the foregoing.

57. The method of claim 56 comprising administering to the subject an immunopotentiating amount of a linear or cyclic dimer or trimer of L-Ile-L-Trp.

58. The method of claim 56 comprising administering to the subject an immunopotentiating amount of L-Ile-L-Trp.

59. A method for enhancing the effect of a vaccination to a disease in a subject comprising the step of administering to the subject an immunopotentiating amount of a dipeptide selected from the group consisting of L-Ile-L-Trp, linear and cyclic monomers and polymers thereof and pharmaceutically acceptable salts of any of the foregoing.

60. The method of claim 59 comprising administering to the subject an immunopotentiating amount of a linear or cyclic dimer or trimer of L-Ile-L-Trp.

61. The method of claim 59 comprising administering to the subject an immunopotentiating amount of L-Ile-L-Trp.

* * * * *

SEQUENCE LISTING ( 1 ) GENERAL INFORMATION:

( i i i ) NUMBER OF SEQUENCES:4

( 2 ) INFORMATION FOR SEQ ID NO:1:

( i ) SEQUENCE CHARACTERISTICS:
        ( A ) LENGTH:2 amino acids
        ( B ) TYPE:AMINO
        ( D ) TOPOLOGY:linear ( i i ) MOLECULE TYPE:peptide ( v i i ) IMMEDIATE SOURCE:

( i x ) SEQUENCE DESCRIPTION: SEQ ID NO:1:

Ile Trp ( 2 ) INFORMATION FOR SEQ ID NO:2:

( i ) SEQUENCE CHARACTERISTICS:
        ( A ) LENGTH:4 amino acids
        ( B ) TYPE:AMINO
        ( D ) TOPOLOGY:linear ( i i ) MOLECULE TYPE:peptide ( v i i ) IMMEDIATE SOURCE:

( i x ) SEQUENCE DESCRIPTION: SEQ ID NO:2:

Ile Trp Ile Trp ( 2 ) INFORMATION FOR SEQ ID NO:3:

( i ) SEQUENCE CHARACTERISTICS:
        ( A ) LENGTH:6 amino acids
        ( B ) TYPE:AMINO
        ( D ) TOPOLOGY:linear ( i i ) MOLECULE TYPE:peptide ( v i i ) IMMEDIATE SOURCE:

( i x ) SEQUENCE DESCRIPTION: SEQ ID NO:3:

Ile Trp Ile Trp Ile Trp ( 2 ) INFORMATION FOR SEQ ID NO:4:

( i ) SEQUENCE CHARACTERISTICS:
        ( A ) LENGTH:8 amino acids
        ( B ) TYPE:AMINO
        ( D ) TOPOLOGY:linear

```
( i i ) MOLECULE TYPE:peptide ( v i i ) IMMEDIATE SOURCE:

( i x ) SEQUENCE DESCRIPTION: SEQ ID NO:4:

Ile  Trp  Ile  Trp  Ile  Trp  Ile  Trp
```